United States Patent [19]

Christman

[11] Patent Number: 4,501,151

[45] Date of Patent: Feb. 26, 1985

[54] ULTRASONIC THERAPY APPLICATOR THAT MEASURES DOSAGE

[75] Inventor: Chris L. Christman, Silver Spring, Md.

[73] Assignee: The United States of America as represented by the Department of Health and Human Services, Washington, D.C.

[21] Appl. No.: 446,408

[22] Filed: Dec. 2, 1982

Related U.S. Application Data

[62] Division of Ser. No. 266,379, May 22, 1981, Pat. No. 4,390,026.

[51] Int. Cl.³ .............................................. G01H 1/00
[52] U.S. Cl. ........................................ 73/646; 128/660
[58] Field of Search .................. 128/736, 804; 73/646; 374/10, 12, 13, 24–30, 43–44, 102, 107, 112–114

[56] References Cited

U.S. PATENT DOCUMENTS

| | | | |
|---|---|---|---|
| 3,392,570 | 7/1968 | Bonjour et al. | 374/12 X |
| 4,166,451 | 9/1979 | Salera | 374/114 X |

Primary Examiner—Kyle L. Howell
Assistant Examiner—Francis J. Jaworski
Attorney, Agent, or Firm—Browdy and Neimark

[57] ABSTRACT

An ultrasonic therapy applicator wherein therapeutic heating is provided by creating a diffuse ultrasonic field in a liquid, such as water, in a tank in which living tissue may be immersed. The diffuse acoustic energy is produced by frequency-modulating the driving ultrasonic frequency in a band employing "white noise" modulation. The apparatus consists of a reverberation tank suspended from a support by four wires. The support is used to mount a transducer, a hydrophone, a specimen holder and a stirrer. The tank is surrounded by a temperature bath. The hydrophone is used for measuring decay rates. The transducer is acoustically matched to the water. Ultrasound is coupled from the transducer via an ellipsoidal vertical reflector vertically aligned below the acoustic window of the transducer. To calibrate integral dosage a temperature sensing probe is used, of the differential temperature analysis type. The probe consists of two thermocouples, one embedded at the center of a RHO-C rubber sphere and the other mounted outside near the sphere. Measuring the differential temperature signal that results when the sphere is irradiated enables determination of the acoustic energy density. The RHO-C rubber has an acoustic impedance nearly equal to that of water, and therefore the probe does not significantly change the exposure field. The absorption coefficient of the rubber is satisfactorily high. Also, the RHO-C rubber holds its thermocouple firmly in place during comparative measurements. The probe minimizes disruption of the exposure and has an omnidirectional response.

11 Claims, 7 Drawing Figures

ULTRASONIC THERAPY APPLICATOR THAT MEASURES DOSAGE

This is a division of application Ser. No. 266,379 filed May 22, 1981, now U.S. Pat. No. 4,390,026.

FIELD OF THE INVENTION

This invention relates to ultrasonic therapy applicators, and more particularly to an applicator which generates a diffuse ultrasonic field and which includes means to measure the applied dosage.

BACKGROUND OF THE INVENTION

Therapeutic heating has long been employed by the medical profession to treat a variety of physical ailments. Currently employed techniques routinely used to heat tissue include microwave diathermy and ultrasonic therapy. Devices now used for therapeutic heating are relatively inexpensive and therefore are widely available (there are approximately 3000 ultrasonic therapy devices sold domestically each year). One serious problem associated with both microwave diathermy and ultrasonic therapy devices is the poor control provided of exposure conditions, namely, dosage. Although the practitioner can specify the exposure time, he still does not know precisely how much actual energy is absorbed by the tissue undergoing treatment, and consequently does not know how high the tissue temperature rise will be. Thus, there is a definite need for an improved exposure system having means for measuring the total ultrasonic energy absorbed by biological tissue undergoing exposure, namely, for therapy applicator apparatus capable of deriving information usable for measuring exposure dosage.

There exists a known technique for measuring the absorption coefficient of liquids below 2.0 MHz (see Karpovich, J.: "Resonance Reverberation Method for Sound Absorption Measurements", J. Acoust. Soc. Am, 16(5), 819–823, 1954; Kurtze, G. and Tamm, K.: "Measurements of Sound Absorption in Water and in Aqueous Solution of Electrolytes", Acustica, 3, 33–48, 1953; Lawley, L. E. and Reed, R. D. C.: "A Reverberation Method for the Measurement of the Absorption of Ultrasonics in Liquids", Acustica, 5, 316–322, 1955; Moen, C. J.: "Ultrasonic Absorption in Liquids", J. Acoust. Soc. Am., 23(1), 62–70, 1951; Mulders, C. E.: "Ultrasonic Reverberation Measurements in Liquids", App.-Sci.Res.,B1, 149–167, 1948). For this technique, a diffuse field is first created in a reverberation tank, and then the time rate of change of acoustic pressure, or decay rate, is determined when the source of ultrasonic energy is modulated. Such a technique has never, however, been applied to the present field.

SUMMARY OF INVENTION

The method employed in the present invention is a modification of the above-mentioned technique which requires that both the decay rate and the total acoustic power delivered by the source be measured.

When relating reverberation measurements to absorbed energy, two basic assumptions are needed: First, the acoustic energy must be diffuse, so that at every point within the field, plane waves have the same average intensity for all directions and phases when averaged over a sufficiently long time in a narrow frequency band. Second, the acoustic energy must be distributed uniformly throughout the liquid. It can be shown that when these conditions are met, the integral dose for the specimen, $\epsilon$, is given by $$\epsilon = Pt(D_s - D_f)/D_s \qquad (1)$$

where P is the total power absorbed within the tank, t is the total exposure time, $D_s$ is the measured decay rate with the specimen in the tank, and $D_f$ is the measured decay rate with the specimen removed.

When deriving equation (1), it is necessary to assume that the uniformity of the energy density, determined with the specimen removed, does not change significantly when the specimen is included. In general, there will be a loss of uniformity of energy density near each surface of the specimen that is related to the loss of energy flux arriving from the direction of that surface. These losses are due to absorption within the specimen of scattering at its interfaces. This effect will not become significant if care is taken to insure that changes in the uniformity of the energy density remain small. In the present invention, two methods are used to minimize these changes: First, a relatively large tank is used such that $D_s$ never becomes larger than 1.5 $D_f$. Second, a reflector is used to improve the diffuseness of the field.

From basic assumptions about a diffuse field and the law of conservation of energy, a differential equation can be derived for the energy density within a reverberation tank. The solution of this equation shows that the energy density decays exponentially with a constant slope given by the decay rate of acoustic pressure within the tank. An expression for the total energy absorbed by the specimen can also be derived that depends on the decay rate with the specimen, the decay rate without the specimen, the total acoustic power absorbed within the tank, and the exposure time.

The method for measuring total absorbed power is based on a conservation of energy equation for the reverberation process. At steady state, when the rate of change of total acoustic energy is zero, the acoustic power supplied by the source equals the total power absorbed within the tank. Therefore, after the energy density in the tank has reached equilibrium, the power delivered by the transducer will determine the total power absorbed in the tank. In general, an amplifier is used to excite the transducer. The cable used to connect them can be represented as a transmission line with a forward electrical wave travelling from the amplifier, and a reflected wave travelling from the transducer. Using this concept, the total power absorbed in the tank at steady state can be expressed as $$P = n'(V_f^2 - V_r^2)/R' \qquad (2)$$

where $n'$ is an efficiency factor that relates electric power to acoustic power, $V_f$ is the voltage of the forward wave, $V_r$ is the voltage of the reflected wave, and $R'$ is the impedance of the transmission line.

An apparatus according to the present invention employs a reverberation tank in which a test specimen may be received, or which may be designed to receive biological tissue to be treated. The tank may be suspended from a rigid support by a suitable number of spaced metal wires to minimize acoustic losses. This support may also be employed to mount a transducer, a mechanical stage carrying a depending hydrophone, the stage having means to adjust the position of the hydrophone in three dimensions, a supporting mechanism for holding a specimen, a thermocouple assembly used for calibration purposes to determine the total acoustic power delivered by the transducer, and a stirrer. For temperature control (thermal regulation), the reverberation tank is suspended inside a second tank which is suitably insulated, for example, lined with polystyrene foam sheets. Water from a temperature bath is circulated between the two tanks to form a thermal jacket around the inner tank. After the temperature has stabilized, the jacket is drained, measurements are taken, and then the thermal jacket is replaced. This enables the temperature within the reverberation tank to be maintained to within about ±0.2° C.

The transducer is excited, using a carrier wave which is frequency-modulated with white noise, which creates a diffuse field in the reverberation tank. The exposure apparatus is specifically constructed to encourage the generation of a diffuse field. This includes suspending the tank from said wires, using degassed water in the associated acoustic coupling assembly, employing a specially-shaped reflector, and embodying a low-loss housing for the transducer. If a diffuse field is created in the reverberation tank, then the integral dose, or total energy absorbed by the specimen, can then be determined by steps including measuring two quantities: (1) the total power P absorbed within the tank, and (2) the decay rate function. Once a diffuse field is created, the integral dose $\epsilon$ is given by Equation (1), namely as a function of total acoustic power P absorbed within the tank, the exposure time t, the decay rate $D_s$ with the specimen included, and the decay rate $D_f$ with the specimen removed.

Accordingly, an object of the invention is to overcome the disadvantage and deficiencies of the previously known therapeutic applicator devices; another object is to provide for improved ultrasonic therapy application.

A furher object of the invention is to provide an improved ultrasonic therapy device which privides a reliable measurement of exposure dosage of the tissue undergoing treatment.

A still further object of the invention is to provide an improved ultrasonic therapy device which furnishes information as to the expected temperature rise of the tissue to be treated.

A still further object of the invention is to provide an improved ultrasonic therapy applicator employing white noise-modulated ultrasonic driving wave energy to generate diffuse ultrasonic excitation, and having structural means to develop substantially uniform energy density in the treatment zone.

A still further object of the invention is to provide an improved ultrasonic therapy applicator having means for measuring dosage in terms of total driving power absorbed within the applicator, total exposure time, decay rate of the excitation wave with the specimen on tissue in the applicator, and the decay rate with the tissue specimen removed, and also having a novel and improved thermocouple means used for calibration purposes to determine the total acoustic power delivered by the ultrasonic driving source.

A still further object of the invention is to provide a novel and improved ultrasonic therapy exposure tank assembly having means to generate a diffuse ultrasonic acoustic field in the assembly, the acoustic field having a substantially uniform energy density throughout the tank assembly, and including apparatus to measure the total acoustic energy or dose which will be absorbed by a specimen placed in the tank assembly, whereby a predetermined dosage of ultrasonic exposure may be delivered to a biological tissue specimen in the tank.

A still further object of the invention is to provide an improved thermal probe for measuring absolute energy density within a diffuse acoustic field, the probe being particularly suited for calibrating ultrasonic therapy equipment of the type which measures integral dosage applied to biological tissue.

A still further object of the invention is to provide an improved thermal probe for measuring ultrasonic energy density within an acoustic exposure tank, being particularly useful for diffuse field measurements, but being also useful for plane wave measurements.

A still further object of the invention is to provide an improved thermal probe of the thermocouple type for measuring ultrasonic energy density within a diffuse acoustic field generated in water, the probe having a substantially omni-directional response, having an acoustic impedance nearly equal to that of water so that it does not significantly change the exposure field, having an absorption coefficient sufficiently high so that detectable temperature rises occur for energy densities of interest, and holding its thermojunction elements substantially rigidly in place during comparative measurements, so that precise results can be obtained.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
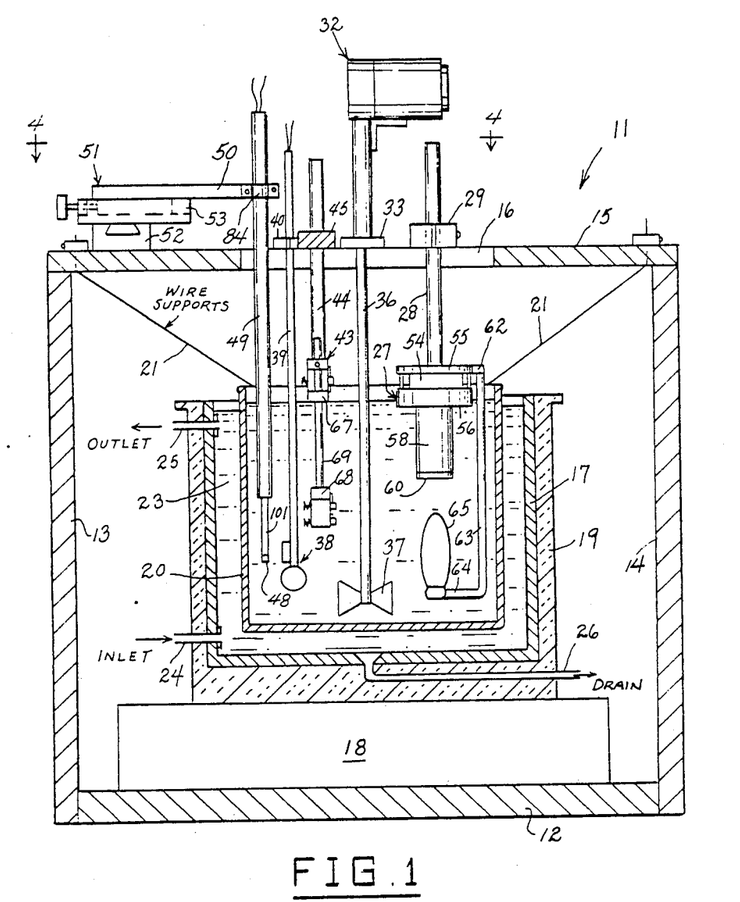
FIG. 1 is a vertical cross-sectional view taken through an improved ultrasonic therapy device constructed in accordance with the present invention.

Referring to the drawings, 11 generally designates an ultrasonic therapy apparatus constructed in accordance with the present invention, designed particularly for exposure of laboratory animals to ultrasonic therapy waves, although it can be modified to accommodate other tissue specimens, including human tissues. The apparatus 11 may comprise a rigid frame structure or enclosure having a base 12, vertical end walls 13, 14, and a generally rectangular top wall 15 having a central aperture 16.

Designated at 17 is an outer tank. Tank 17 is provided with a heat-insulating outer lining 19 of suitable thermally insulating material, such as polystyrene foam, which may be either in solid or sheet form. The heat-insulated tank 17 is mounted on a supporting block 18. A cylindrical reverberation tank 20 is suspended in the tank 17 by means of respective support wires 21 connecting 90°-spaced apertured lugs 22 on the rim portion of tank 20 to the corner portions of rectangular top wall 15. This defines a space 23 between inner tank 20 and the outer tank 17. Water from a temperature-controlled bath may circulate through the jacket space 23 via a bottom inlet conduit 24 and a top outlet conduit 25. The water in the jacket space 23 may be at times drained from said space via a normally closed-off drain conduit 26.

A transducer assembly 27 is provided with a top suspension rod 28 which is adjustably clamped to the inner end portion of a horizontal supporting bar 29. Bar 29 is in turn adjustably clamped to top wall 15 by a clamping screw 30 engaged through a longitudinal slot 31 in bar 29 and threadedly engaged in top cover 15 (see FIG. 4), enabling horizontal pivotal and horizontal longitudinal adjustment of bar 29, as well as vertical adjustment of transducer assembly 27 in tank 20.

A stirrer assembly 32 is secured on the inner end portion of a horizontal supporting bar 33 adjustably secured to top plate 15 by a clamping screw 34 engaged through a longitudinal slot 35 in bar 33 and threadedly engaged in plate 15. The stirrer assembly 32 has a vertical shaft 36 extending into tank 20 and having stirrer blades 37 on its lower end.

A thermocouple temperature probe assembly 38 also extends into tank 20 and is provided with a vertical supporting tube 39 which is adjustably clamped to the inner end portion of a horizontal supporting bar 40, which is in turn adjustably secured to plate 15 by a clamping screw 41 engaged through a longitudinal slot 42 in bar 40 and threadedly engaged in plate 15.

A holding mechanism 43 to support a test specimen in tank 20 is provided with a vertical supporting rod 44 which is adjustably clamped to the inner end portion of a horizontal supporting bar 45, which is in turn adjustably secured to top plate 15 by a clamping screw 46 engaged through a longitudinal slot 47 in bar 45 and threadedly engaged in plate 15.

A hydrophone 48 is secured to the bottom end of a small hollow tube 101, which in turn is secured to the bottom end of a vertical supporting member 49, which is adjustably clamped at 84 to the inner end portion of a horizontal supporting bar 50 forming part of an adjustable stage assembly 51 mounted on top plate 15. The stage assembly 51 has cooperating bottom and upper dove-tailed block portions 52, 53 for transverse adjustment of the hydrophone, and the bar 50 is likewise dovetailed to upper block portion 53 for longitudinal adjustment. Thus, the hydrophone is adjustable in three dimensions in tank 20.

The transducer assembly 27 (FIG. 2) comprises a suitable high power transducer unit 54 of a commercially available type which consists of a PZT ceramic disc with a diameter of 2.54 cm and a resonant frequency of 1.0 MHz, in a typical embodiment. This is mounted inside a cylindrical housing which has a diameter of 10 cm and a length of 3.5 cm. The ceramic is acoustically matched to water through an aluminum plate, and is also electrically matched to 50 ohms and has a 3. dB bandwidth of 285 kHz. Ultrasound is coupled from the transducer unit 54 to the reverberation tank 20, employing the assembly shown in FIG. 2. The transducer unit 54 is sandwiched between a solid upper plate 55 and a hollow lower plate 56, which are held together by a plurality of circumferentially-spaced screws 57. The suspension rod 28 is rigidly secured centrally to the top plate 55, to suspend the assembly in the tank 20. The hollow bottom plate 56 is fitted with an axially depending cylindrical extension 58, which in said typical embodiment is 3.5 cm in diameter and 7.5 cm in length, forming a reservoir which is sealed at its top end by an O-ring 59 interposed between transducer unit 54 and the top surface of plate 56, and sealed at its bottom by a thin acoustically transparent polyvinylidene chloride membrane 60 clamped to the bottom rim of extension 58. The reservoir is filled from the bottom with degassed distilled water 61 before the membrane 60 is stretched into place, care being taken to insure that no air bubbles are trapped in the reservoir before the assembly 27 is lowered into the tank 20.

Figures 2, 3:
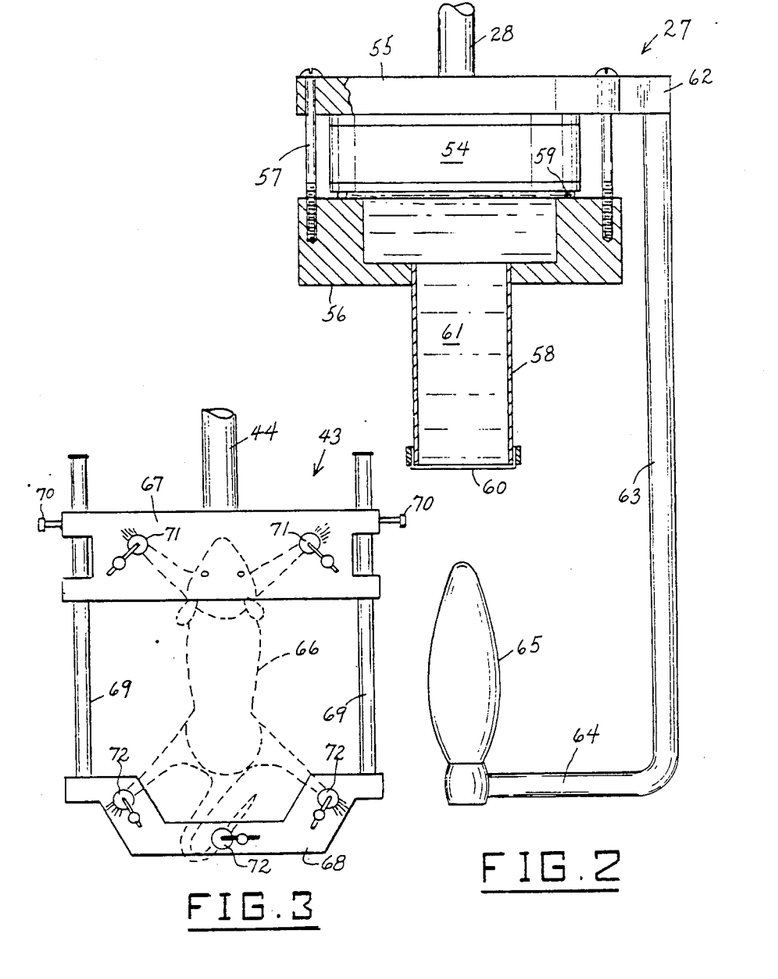
FIG. 2 is an enlarged elevational view, partly in vertical cross-section, of the transducer mounting assembly employed in the ultrasonic therapy device of FIG. 1.
FIG. 3 is an enlarged front elevational view of a typical test specimen holding mechanism employed with the ultrasonic therapy device of FIG. 1.

The top plate 55 has an integral peripheral radial lug 62 to which is rigidly secured a depending reflector support rod 63 formed with a horizontal bottom support arm 64 on which is rigidly mounted, in axial alignment with reservoir extension 58, an upstanding acoustic reflector 65, of substantially ellipsoidal shape, spaced about 4.5 cm below the membrane 60. Reflector 65 consists of an evacuated glass vessel with a maximum diameter of 3 cm and a length of 7 cm. The reflector is used to produce a highly diffuse acoustic field, and the assembly 27 is designed to couple acoustic energy from the transducer unit 54 to the reverberation tank 20, while minimizing losses within the transducer housing.

Therefore, acoustic losses in the reverberation apparatus are minimized, firstly, by suspending the tank 20 from the support plate 15 using metal wires 21, as previously described, and secondly, by using the above described low-loss transducer assembly. Ideally, any acoustic energy incident on a wall surface of the tank 20 is totally reflected, creating a diffuse field within the tank. The reflector 65 is also designed to produce a diffuse field by scattering the direct wave produced by the transducer unit 54.

The specimen holding mechanism 43, shown in detail in FIG. 3, is suitably designed to hold a test specimen, such as a live test animal 66, with the major portion of its body immersed in the water irradiated with ultrasonic acoustic energy in the reverberation tank 20. For example, the holding mechanism may comprise a top horizontal arm 67 rigidly connected at its midportion to the lower end of rod 44. The bottom arm 68 has vertical upstanding support rods 69, 69 rigidly connected to its respective ends, which engage through the opposite end portions of top arm 67 and are adjustably fastened thereto by clamping screws 70, 70. The top arm 67 is provided with spring clips 71, 71 adapted to clampingly engage the animal's front legs, and the bottom arm 68 is similarly provided with spring clips 72 adapted to clampingly engage with the animal's rear legs and tail, as shown in FIG. 3, whereby to secure the animal to the holder in a humane manner and without inflicting serious injury to the animal.

Figures 4, 5, 6:
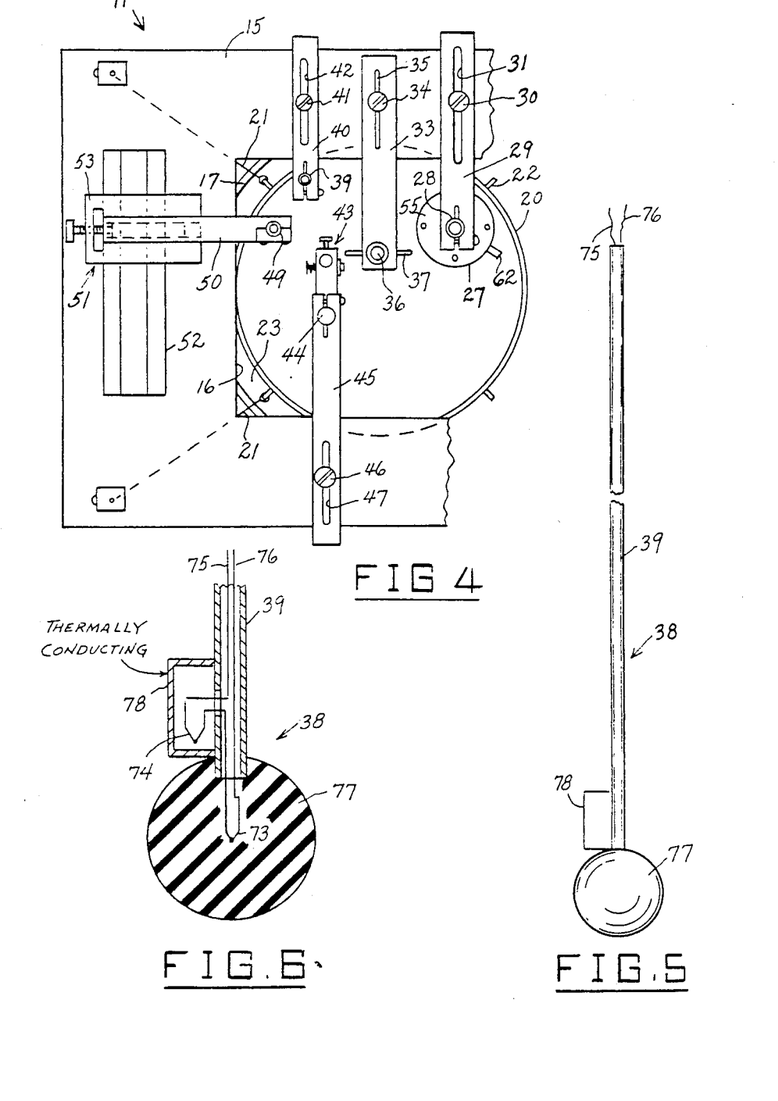
FIG. 4 is a fragmentary horizontal sectional view taken substantially on the line 4—4 of FIG. 1.
FIG. 5 is an enlarged elevational view of the thermal probe assembly employed in the device of FIG. 1.
FIG. 6 is an enlarged vertical cross-sectional view taken through the lower portion of the thermal probe assembly of FIG. 5.

The thermocouple temperature probe assembly 38 comprises two thermocouples 73, 74, connected to define a circuit of the differential temperature analysis type, namely, differentially in series with lead wires 75, 76 extending through the support tube 39. The thermocouple 73 is embedded at the center of a RHO-C rubber sphere 77, and the thermocouple 74 is mounted in a thermally conducting protective housing 78 secured to the lower end portion of tube 39 outside the spherical rubber ball 77 but adjacent thereto. Measuring the differential temperature that results when the sphere 77 is irradiated determines the acoustic energy density. The RHO-C rubber has an acoustic impedance nearly equal to that of water, and therefore the probe 38 does not significantly change the exposure field. The absorption coefficient of the rubber is satisfactorily high. Also, the RHO-C rubber holds thermocouple 73 rigidly in place during comparative measurements. The probe 38 minimizes disruption of the exposure and has a substantially omnidirectional response. Said probe is used for calibration purposes to determine the total acoustic power delivered by the source 54. This quantity, the decay rate with the specimen, the decay rate with the specimen removed, and the total exposure time, provide all the information needed to measure the total energy absorbed.

Methods previously employed to measure the total power P absorbed in the tank at steady state according to Equation (2) are valid for a free-field exposure condition but are not valid for a diffuse field exposure condition. Therefore, a different method must be used to determine the absolute power absorbed within the tank 20. Because the temperature rise is fundamentally related to absorbed energy, measuring the temperature rise within the tank can be used to determine the energy density within the tank, which in turn is related to the power delivered by the transducer 54. The thermocouple 73, which may be a copper constantan junction, at the center of the rubber ball 77, acts as the main active component, while the second copper constantan junction thermocouple 74 is used as the reference junction. Since the probe 38 has substantially spherical geometry, it has a substantially omnidirectional response.

Although the probe 38 is employed herein to calibrate the measurement of integral dose, it can also be used to determine a transducer's output power for any diffuse field exposure condition. Thus, the probe is useful in many ultrasonic cleaning applications. in addition, the probe can respond to plane wave exposure conditions, and may be useful for free-field calibration as well as in diffuse field exposure conditions.

In the typical embodiment, the RHO-C rubber sphere 77 was 20 mm in diameter. The RHO-C rubber (available from the B. F. Goodrich Co.) is prepared by heating a mixture of the curing agent and base compound (15 g of the curing agent to 100 g of the base compound) to 100° C. and then letting it cure for 24 hours. The bubbles that are not removed by heating are removed by vacuum during this curing process. Both thermocouples 73, 74 have copper constantan junctions and are fabricated by lap-soldering two different 0.07 mm diameter thermocouple wires together.

RHO-C rubber was chosen as the absorbing material because its acoustic impedance is nearly equal to the acoustic impedance of water. Therefore the probe does not significantly change the exposure field. The absorption coefficient of RHO-C rubber is also ideally suited for this type of probe. The absorption coefficient is high enough so that detectable temperature rises occur for energy densities of interest ($10^{-5}$ J/cm$^3$). Another advantage of the RHO-C rubber is that it holds the thermocouple 73 rigidly in place during comparative measurements, so that precise results can be obtained.

To calibrate the apparatus for measuring the total acoustic power P, a standard technique may be used which involves measuring the temperature rise within the absorbing material. The calibration procedure may comprise the following steps:

1. The spatial peak temporal average acoustic intensity is determined by a standard method, with the probe 38 placed in an anechoic (non-reflective) tank. This method may be the ball deflection method described in Dunn et al, Acustica 38, 58–61, 1977; Hasegawa et al, J. Acoust. Soc. Japan, 30, 443–448, 1974; Hasegawa et al, J. Acoust. Soc. Am. 58, 581–585, 1975.

2. With the thermocouple probe's junction positioned where the intensity was determined, its voltage response is recorded as a function of time for a known intensity.

3. The probe 38 is then transferred to the reverberation tank 20, and then its voltage response is again recorded.

4. The total power P delivered by the transducer 54 can then be determined from the time rate of change of the probe's voltage response in the non-reflecting tank, the time rate of change of the probe's voltage response in the reverberation, tank 20, and the known acoustic intensity in the non-reflecting tank.

The output of the probe 38 can therefore be employed for the derivation of a signal representing the total power P absorbed within the tank, which in turn can be employed in Equation (1) to determine the integral dose $\epsilon$ for the specimen. In actual practice, probe 38 is used to determine the efficiency of the transducer (Equation 2) while the total power P absorbed within the tank is routinely measured by determining the electrical power delivered to the transducer.

Figure 7:
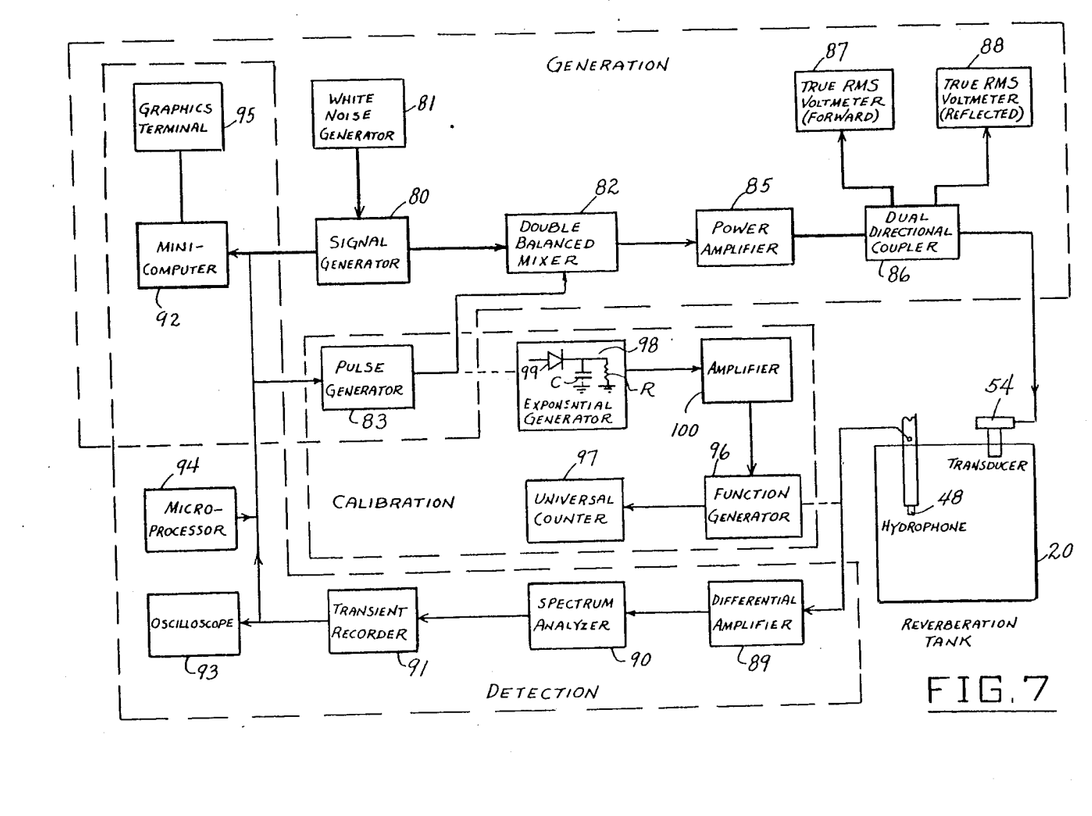
FIG. 7 is a block diagram of an electrical system employed for measuring decay rate, in association with the ultrasonic therapy device of FIG. 1.

Now that the method for measuring the total absorbed power P has been generally explained, the method and apparatus for measuring the decay rates $D_s$ and $D_f$ will be described. FIG. 7 is a block diagram of the system employed for measuring said decay rates. It is divided into three sections, each representing a different function performed, namely: generation, detection, and calibration. Some of the components appear in two sections because they are employed in the performance of two of said functions.

Ultrasound is produced using a signal generator 80 with a center frequency of 1.0 MHz which is frequency-modulated by a pseudo-random white noise generator 81, which may be similar to the commercially available Grason-Stadler Model 1724. In a typical case an acoustic 3-dB bandwidth was produced, which was 285 kHz, or approximately 30% of the source frequency. This signal was found to be sufficient to create a diffuse acoustic field. Thus, this technique improves the uniformity of the acoustic energy density produced within the tank 20, and operates by breaking up the standing wave pattern which normally occurs for a single-frequency excitation. Bursts of RF are produced by gating a double balanced mixer 82 with a square wave whose period 1s 112 ms, from a pulse generator 83. The output of mixer 82 is amplified in a power amplifier 85 and is applied to the transducer 54 via a dual directional coupler 86 which is used to measure the electrical power delivered to the transducer. Each channel of the coupler 86 is connected to a true RMS voltmeter, shown respectively at 87 and 88. The output of the hydrophone 48, which responds to the acoustic pressure within the tank 20, is first amplified in a differential amplifier 89 and the detected by a spectrum analyzer 90 set for wide band operation. The logarithmic output from the spectrum analyzer 90 is captured by a transient recorder 91 and then transferred to a minicomputer 92 for later analysis. An oscilloscope 93 may be employed to display the decay of the acoustic pressure as a function of time, which is stored by the transient recorder 91.

A microprocessor 94 controls the synchronization of each measurement cycle by producing a signal every 112 ms, which triggers the pulse generator 83. When this happens, the transducer 54 is gated off and the acoustic pressure within the tank 20 begins to decay. At the same time, another signal arms are triggers the transient recorder 91 so that the decay curve will be stored in its memory. After 40 ms, the transducer 54 is switched on again, allowing the acoustic energy density within the tank 20 to build up and reach equilibrium before the next cycle begins. This process is repeated continuously, until the minicomputer 92 requests data from the transient recorder 91, at which time the microprocessor 94 inhibits the normal measurement cycle unitl an entire data block, representing one decay curve, has been transferred.

The microcomputer 92 calculates the decay rate using a decay rate averaging method (DCAM). An averaging procedure is necessary because random fluctuations inherent in the reverberation process cause considerable scatter in any single decay curve. To reduce this scatter, a smoothed decay curve is generated using the procedure outlined below. The points from 16 individual decay curves are averaged and then converted to coordinates of acoustic pressure in dB and time in ms, using an amplitude calibration constant and a time base calibration constant. This smoothed decay curve is then plotted on a graphics display terminal 95, connecting individual points by straight line segments. A linear regression analysis is used to measure the slope of the decay curve to determine the decay rate. By plotting the regression line on top of the smoothed decay curve, the regression limits can be adjusted to obtain the best fit. Using this procedure, a single value for the decay rate can be obtained in less than 30 seconds.

The calibration constants for the DCAM are determined before each experiment. To do this, a function generator 96, producing a square wave whose period has been accurately measured using a universal counter 97, is at that time drivingly connected to the transient recorder 91. The time base calibration constant is calculated from the period of the square wave and the time interval needed to display one complete cycle. Since the time interval determined by the transient recorder 91 represents a discrete number, there will be, in general, a small digitizing error associated with round-off. To calibrate the amplitude scale of the transient recorder 91, the pulse generator 83 is first disabled, producing a horizontal decay curve. By switching the video filter of the spectrum analyzer 90, normally set at 10 kHz, to 100 Hz, this curve can be made extremely flat. Its position is changed using a calibrated attenuator which is built into the spectrum analyzer 90. The amplitude calibration constant is determined by recording the change in position of this decay curve in 10 dB steps over a range of at least 30 dB.

Although the calibration procedure outlined above is useful for determining both the amplitude and time scales for the transient recorder 91, it does not provide an absolute calibration of the system. To do this, a technique routinely used for calibration in reverberation measurements is employed which uses a parallel R-C network 98 to produce a known decay rate (see Mulders, C. E., "Ultrasonic Reverberation Measurements in Liquids", Appl. Sci. Res., B1, 149–167, 1948; Hunter, G. H. and Lawson, M. V., "Reverberation Time Measurements of the Scattering of Sound by Turbulence", J. Acoust. Soc. Am., 55(5), 937–940, 1974). The dashed lines in the block diagram of FIG. 7 show the connections which are needed to measure the decay rate for this simulated signal. Referring to said block diagram, a positive pulse from the pulse generator 83 charges the capacitor C through the diode 99. When the pulse ends, the diode 99 isolates the R-C network from the pulse generator, and the voltage across the capacitors C begins to decay exponentially with a decay rate determined by R and C. This voltage is then amplified in an amplifier 100 and added to a DC offset to make it compatible with the modulation circuitry of the function generator 96. The output from the function generator 96 consists of a 1.0 MHz carrier wave which has an exponentially decaying envelope. This signal is used to simulate a decay curve produced in the reverberation tank 20, and its decay rate in dB/sec is given by 20 log(e) times the product of RC. In practice, precision substitution boxes are used for both R and C.

Summarizing, the above describes an ultrasonic applicator that measures integral dose. The instrument comprises a reverberation chamber or tank 20, a transducer 54, a hydrophone 48, and associated electronics. If a diffuse field can be created in the reverberation tank, then the integral dose, or total energy absorbed by the specimen, can be determined by measuring two quantities: the total power P absorbed within the tank, and the decay rate. The exposure apparatus is specifically constructed to encourage the generation of a diffuse field. Suspending the tank from wires 21, using degassed water, employing a reflector 65, and providing a low-loss housing for the transducer 54 all help to achieve this goal. In addition, the transducer 54 is excited using a carrier wave which is frequency-modulated with white noise.

Once a diffuse field is created, the integral dose of the specimen is determined from the total acoustic power P absorbed within the tank, the exposure time t, the decay rate $D_S$ with the specimen included, and the decay rate $D_f$ with the specimen removed, according to Equation (1). For this device, the actual total acoustic power absorbed within the tank is measurable from the electrical power dissipated by the transducer and the transducer's efficiency. The transducer's efficiency is calibrated using the thermocouple temperature probe 38. In general, this efficiency will change as the transducer is moved to different positions within the tank 20.

To measure the decay rate, the automated system of FIG. 7 can be employed. This system records the exponential decay of acoustic pressure within the tank, linearizes the decay by scaling, and then determines the slope of each individual decay curve. The decay rate is given by the average slope of several different decay curves. Procedures are also available for calibrating the measurement of decay rate.

While a specific embodiment of an improved ultrasonic therapy applicator with means to measure the applied dosage has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A thermal probe for measuring ultrasonic energy density within an acoustic exposure receptacle containing liquid, comprising an elongated support, a body of acoustically absorbing material secured to an end portion of the elongated support, said body being so configured as to interact with said ultrasonic energy in an omnidirectional manner, a first thermocouple mounted in the interior of said acoustically absorbing body, a reference thermocouple mounted on said support adjacent to and outside of said body; means to permit said body of acoustically absorbing liquid together with said first thermocouple therein, said reference thermocouple and the adjacent position of said support to function when immersed in said liquid; and circuit means differentially connecting the two thermocouples.

2. The thermal probe of claim 1, and means to mount said elongated support in a substantially upright position in a receptacle.

3. The thermal probe of claim 1, and wherein said acoustically absorbing material is non-metallic and is substantially acoustically transparent when immersed in said liquid.

4. The thermal probe of claim 1, and wherein said body of acoustically absorbing material comprises RHO-C rubber.

5. The thermal probe of claim 1, and wherein said acoustically absorbing body is substantially spherical and said first thermocouple is embedded substantially centrally in said body.

6. The thermal probe of claim 1, and wherein said acoustically absorbing material has an acoustic impedance approximately equal to that of water.

7. The thermal probe of claim 1, and wherein said body of acoustically absorbing material comprises a spherical ball of RHO-C rubber and wherein said first thermocouple is embedded substantially centrally in said spherical ball.

8. A thermal probe for measuring ultrasonic energy density within an acoustic exposure receptacle containing liquid, comprising an elongated support, a body of acoustically absorbing material secured to an end portion of the elongated support, a first thermocouple mounted in the interior of said acoustically absorbing body, a reference thermocouple mounted on said support adjacent to and outside of said body, circuit means differentially connecting the two thermocouples, and wherein said acoustically absorbing material is non-metallic and is substantially acoustically transparent when immersed in said liquid.

9. The thermal probe of claim 8, and wherein said body of acoustically absorbing material comprises RHO-C rubber.

10. A thermal probe for measuring ultrasonic energy density within an acoustic exposure receptacle containing liquid, comprising an elongated support, a body of acoustically absorbing material secured to an end portion of the elongated support, a first thermocouple mounted in the interior of said acoustically absorbing body, a reference thermocouple mounted on said support adjacent to and outside of said body, circuit means differentially connecting the two thermocouples, and wherein said acoustically absorbing material has an acoustic impedance approximately equal to that of water.

11. The thermal probe of claim 10, and wherein said body of acoustically absorbing material comprises a spherical ball of RHO-C rubber and wherein said first thermocouple is embedded substantially centrally in said spherical ball.

* * * * *